US010773037B2

(12) United States Patent
Adametz et al.

(10) Patent No.: US 10,773,037 B2
(45) Date of Patent: Sep. 15, 2020

(54) VENTILATOR AND METHOD

(71) Applicant: Loewenstein Medical Technology S.A., Luxembourg (LU)

(72) Inventors: Benjamin Adametz, Hamburg (DE); Marcel Mehnert, Kremperheide (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 348 days.

(21) Appl. No.: 15/627,591

(22) Filed: Jun. 20, 2017

(65) Prior Publication Data

US 2017/0368277 A1  Dec. 28, 2017

(30) Foreign Application Priority Data

Jun. 23, 2016 (DE) .................... 10 2016 007 659

(51) Int. Cl.
*A61M 16/00* (2006.01)
*A61M 16/20* (2006.01)

(52) U.S. Cl.
CPC .... *A61M 16/0066* (2013.01); *A61M 16/0051* (2013.01); *A61M 16/0069* (2014.02);
(Continued)

(58) Field of Classification Search
CPC ... A61B 5/0402; A61B 5/0476; A61B 5/0488; A61B 5/0496; A61B 5/085; A61B 5/087; A61B 5/113; A61B 5/145; A61B 5/14535; A61B 5/4818; A61M 16/0006; A61M 16/0051; A61M 16/0069; A61M 16/024; A61M 16/06; A61M 16/0633; A61M 16/0638; A61M 16/0655; A61M 16/0677;
(Continued)

(56) References Cited

U.S. PATENT DOCUMENTS 4,621,632 A * 11/1986 Bartels .............. A61M 16/1075
128/203.17
4,682,010 A * 7/1987 Drapeau ........... A61M 16/1075
128/203.27
(Continued)

FOREIGN PATENT DOCUMENTS

DE   102014012805 A1   3/2016
EP       2153857 A2    2/2010
WO    2010067236 A1    6/2010

*Primary Examiner* — Annette Dixon
(74) *Attorney, Agent, or Firm* — Abel Schillinger, LLP (57) ABSTRACT

The present invention relates to a method for protecting a ventilation device of a ventilator against backflowing exhaled air, and to a ventilator. A respiratory gas flow is generated by a blower device and is guided via a flow connection to a breathing interface. The respiratory gas flow is adjusted with the aid of a control device to a first ventilation pressure during an inhalation phase of the patient and to a second ventilation pressure during an exhalation phase. A characteristic variable for a flow within the flow connection is detected by a device for monitoring backflowing exhaled air. A back pressure with respect to the backflowing expiratory flow is adjusted by a specific increase of the ventilation pressure taking into consideration the characteristic variable, whereby an undesirable rebreathing into the ventilation device is counteracted by the back pressure.

19 Claims, 2 Drawing Sheets

(52) U.S. Cl.
CPC .......... *A61M 16/20* (2013.01); *A61M 16/205* (2014.02); *A61M 2016/003* (2013.01); *A61M 2016/0027* (2013.01); *A61M 2016/0042* (2013.01); *A61M 2205/15* (2013.01); *A61M 2205/18* (2013.01); *A61M 2205/3334* (2013.01); *A61M 2205/3365* (2013.01)

(58) Field of Classification Search
CPC .......... A61M 16/0683; A61M 16/0694; A61M 16/08; A61M 16/0808; A61M 16/0825; A61M 16/0841; A61M 16/0858; A61M 16/0875; A61M 16/107; A61M 16/1075; A61M 16/1085; A61M 16/109; A61M 16/1095; A61M 16/12; A61M 16/16; A61M 16/164; A61M 2016/0021; A61M 2016/0024; A61M 2016/0036; A61M 2016/0039; A61M 2202/0007; A61M 2202/0078; A61M 2202/0208; A61M 2202/03; A61M 2202/20; A61M 2205/0205; A61M 2205/0238; A61M 2205/3368; A61M 2205/368; A61M 2205/502; F16L 11/12; F24H 3/0405; F24H 9/2071; Y10T 428/26
See application file for complete search history.

(56) References Cited

U.S. PATENT DOCUMENTS

| | | | |
|---|---|---|---|
| 5,558,086 A * | 9/1996 | Smith | A61M 16/0677 128/204.26 |
| 6,564,798 B1 | 5/2003 | Jalde | |
| 2008/0032119 A1* | 2/2008 | Feldhahn | A61M 16/06 428/332 |
| 2008/0078386 A1* | 4/2008 | Feldhahn | A61M 16/06 128/204.18 |
| 2009/0107498 A1* | 4/2009 | Plattner | A61M 16/024 128/204.23 |
| 2011/0226248 A1 | 9/2011 | Duff et al. | |
| 2012/0024286 A1 | 2/2012 | Boring | |
| 2014/0150793 A1 | 6/2014 | Douglas et al. | |

* cited by examiner

VENTILATOR AND METHOD

CROSS-REFERENCE TO RELATED APPLICATIONS

The present application claims priority under 35 U.S.C. § 119 of German Patent Application No. 10 2016 007 659.3, filed Jun. 23, 2016, the entire disclosure of which is expressly incorporated by reference herein.

BACKGROUND OF THE INVENTION

1. Field of the Invention

The present invention relates to a method for protecting a ventilation device of a ventilator against backflowing exhaled air and to a ventilator comprising at least one ventilation device including at least one blower device for generating a respiratory gas flow.

2. Discussion of Background Information

The ventilation of patients is generally adapted to the individual needs of the patient. Frequently, a decision must be made in this case between leakage ventilation or valve ventilation.

In valve ventilation, a tubing system including a controlled exhalation valve is generally utilized. The exhalation valve is closed during inhalation and is usually open during exhalation. In this case, the exhaled air can flow into the surroundings via the valve.

However, the exhaled air frequently also flows back into the ventilation tube during exhalation. Rebreathing can occur in this case, which takes place beyond the ventilation tube and into the ventilator. A particularly problematic aspect thereof is that the rebreathing can also result in germs entering the device.

In the prior art, a non-return valve is installed at the device inlet port. This valve closes off the device when the pressure of the respiratory gas flow drops so far that rebreathing into the device could occur.

Such non-return valves often require that time-consuming conversions of the ventilator be carried out when there is to be a switch between a tubing system with leakage ventilation and a tubing system with valve ventilation. This is a great disadvantage in the case of clinical devices, since switches are frequently carried out with such devices and implementing the conversions therefore takes up a substantial amount of time.

The conversion work with respect to the non-return valve generally has disadvantages in the case of home therapy devices as well. For example, the exchange requires an expensive visit by a technician. The exchange process can also be technically designed in such a way that it can be reliably carried out by inexperienced users. Many users often consider the conversion work to be burdensome, however.

In view of the foregoing, it would be advantageous to have available a method and a ventilator which offer protection against backflowing exhaled air and which are also particularly user-friendly. In particular, it would be advantageous if a convenient switch between leakage ventilation and valve ventilation were possible without requiring conversions.

SUMMARY OF THE INVENTION

The present invention provides a method and a ventilator as set forth in the instant independent claims. Refinements and advantageous designs thereof are the subject-matter of dependent claims.

The method according to the invention is used for protecting a ventilation device of a ventilator against backflowing exhaled air. At least one respiratory gas flow is generated by means of at least one blower device and is guided via at least one flow connection to a breathing interface. The respiratory gas flow is adjusted with the aid of at least one control device to at least one first ventilation pressure during an inhalation phase of the patient. The respiratory gas flow is adjusted to at least one second ventilation pressure during an exhalation phase. At least one characteristic variable for a flow within the flow connection is detected in this case in order to monitor the backflowing exhaled air. The monitoring takes place by means of at least one monitoring device. At least one back pressure with respect to the backflowing expiratory flow is adjusted by means of a specific increase of the ventilation pressure with consideration for the detected variable. An undesirable rebreathing into the ventilation device is counteracted by means of the back pressure.

The method according to the invention has many advantages. One substantial advantage may be that the protection against backflowing exhaled air takes place by means of a back pressure which is built up by the blower device. As a result, a non-return valve for preventing rebreathing into the ventilation device can be dispensed with. The method according to the invention therefore allows for a particularly user-friendly and convenient switch between leakage ventilation and valve ventilation, since no conversions with respect to a non-return valve need to be carried out.

Within the scope of the present invention, a back pressure is understood to mean, in particular, a pressure which is equal to or greater than the pressure of backflowing exhaled air, and so the back pressure prevents the flow of exhaled air into the tubing device.

It is possible that the second ventilation pressure is less than the first ventilation pressure. It is also possible that the second ventilation pressure is greater than the first ventilation pressure. In particular, the second ventilation pressure is specifically increased to the back pressure only intermittently. It is also possible that the second ventilation pressure is increased to the back pressure during its entire duration.

It is possible that the back pressure is less than the first ventilation pressure. It is also possible that the back pressure is greater than the first ventilation pressure. In particular, the back pressure is increased only intermittently. It is also possible that the back pressure at least intermittently corresponds to the second or the first ventilation pressure.

Particularly preferably, a volumetric flow rate is detected as the characteristic variable for the flow. A volumetric flow rate is particularly suitable for monitoring a backflowing expiratory flow. It is also possible that a flow rate and/or a mass flow rate and/or a flow direction are/is detected as the characteristic variable for the flow. A pressure may also be detected. In particular, a patient's expiratory flow that is flowing back into the flow connection may be monitored.

Preferably, the level and/or the duration of the back pressure and/or the point in time of the generation of the back pressure are/is adjusted with consideration for the detected variable. Such an adjustment depending on the detected variable makes it possible to achieve a particularly specific adjustment of the back pressure. For example, the level of the back pressure is adjusted in such a way that it is greater than or equal to the pressure of the backflowing exhaled air. The back pressure is adjusted, in particular, by adjusting the blower speed of the blower device.

It is also possible that the back pressure is adjusted to a pressure which is greater than the pressure of the backflowing exhaled air by a certain factor. The factor is preferably selected in such a way that a backflow into a tubing device is possible, but the exhaled air does not enter the ventilation device. The duration of the back pressure is preferably adjusted in such a way that a backflow into the ventilation device is counteracted up to the end of the particular exhalation phase. The point in time of the generation of the back pressure may be adjusted, in particular, in such a way that the backflowing exhaled air is hindered by the back pressure at the latest when the backflowing exhaled air would enter the ventilation device.

In particular, the back pressure is applied when the detected variable indicates there is a flow within the flow connection that is below at least one threshold value. The threshold value preferably defines a deceleration of the respiratory gas flow generated by the blower device, which results in rebreathing into the ventilation device.

The back pressure may also be applied when the detected variable indicates a negative flow. It is also possible that the back pressure is applied when the detected variable indicates there is a flow standstill—within the flow connection—of the respiratory gas flow generated by the blower device. A negative flow is characterized, in particular, in that the flow direction extends from the breathing interface in the direction of the blower device.

It is possible that the back pressure is applied after at least one latency. The latency preferably defines the flow duration of the backflowing expiratory flow through a tubing device coupled to the ventilation device. In particular, the flow duration of the backflowing expiratory flow is dependent not only on the dead space volume, but also on the flow rate or the flow pressure. The flow rate or the flow pressure is preferably detected by the monitoring device and, particularly preferably, on the basis of the characteristic variable.

Such a latency has the advantage that the back pressure does not need to be maintained, for example, during the entire exhalation phase. As a result, the influence of the back pressure on ventilation is kept particularly low and, at the same time, effective protection of the ventilation device against contamination is ensured. An entry by the backflowing expiratory flow into the tubing device is generally unproblematic in terms of contamination, since the tubing devices are either one-way systems or they can be easily cleaned.

It is also possible that the latency defines a time period up to the arrival of the backflowing expiratory flow at a position of the flow connection to be protected. The position of the flow connection to be protected is preferably located, in particular, at a fixedly installed device section in the interior of the ventilation device.

The latency preferably begins at a point in time when the detected variable indicates there is a negative flow and/or when a threshold value for the flow is fallen below. A negative flow comprises, for example, a respiratory gas component and an exhaled air component. The detection of a negative flow on the basis of the characteristic variable generally initially indicates there is a backflow of the respiratory gas component. The latency preferably begins at this point in time. If the exhaled air component now reaches the critical areas of the flow connection and, for example, the device section, the latency has elapsed and the back pressure is applied. In this way, contaminated exhaled air is effectively prevented from entering the ventilation device.

The latency is preferably dynamically calculated by the monitoring device. In particular, a dead space volume of a connected tubing device, which is stored in the monitoring device, is taken into consideration in this case. Preferably, at least one value of the negative flow is also taken into account. The value of the negative flow is preferably the flow rate and/or the flow pressure and/or, particularly preferably, the volumetric flow rate. By means of such a calculation of the latency, the application of the back pressure can be specifically adapted to the tubing device utilized and to the backflow. The backflow depends, for example, on the exhalation activity of the patient and on the second ventilation pressure during the exhalation phase. The second ventilation pressure other than the increase to the back pressure is adjusted, for example, with consideration for a PEEP (positive end-expiratory pressure) or an EPAP (expiratory positive airway pressure).

In all embodiments, it is particularly preferred that the ventilator is operated in an operating mode for valve ventilation. For this purpose, at least one exhalation valve is opened, in particular during the exhalation phase of the patient, in order to discharge exhaled air. The second ventilation pressure is preferably also used for flushing exhaled air out of a breathing interface. The exhalation valve is preferably at least partially open during the exhalation phase and/or during the second ventilation pressure.

In particular, the ventilator comprises at least one tubing device comprising a controllable exhalation valve. The ventilation device is suited and designed, in particular, for controlling the exhalation valve and, in particular, for controlling via a PEEP control pressure and/or an EPAP control pressure.

The method is particularly advantageous in such an embodiment, since rebreathing into the tubing device frequently occurs during valve ventilation and, therefore, rebreathing into the ventilation device can also occur. In the case of valve ventilation in the prior art, a non-return valve is therefore generally provided between the tubing device and the ventilation device. In the case of valve ventilation, the non-return valve can therefore be dispensed with due to the application of the back pressure.

It is also possible that the ventilator is operated in an operating mode for leakage ventilation. In such a mode, back pressure is preferably not generated. It can also be provided, however, that a continuous ventilation pressure is intermittently increased to the back pressure. It is also possible, however, that in a mode for leakage ventilation as well, a first and a second ventilation pressure are also provided and the second ventilation pressure is increased to a back pressure or a back pressure is additionally provided.

In particular, the degree of opening of the exhalation valve is controllable. The degree of opening of the exhalation valve is preferably controlled by means of the monitoring device. In particular, the control also includes regulating. In particular, the degree of opening of the exhalation valve is controllable via a PEEP control pressure and/or an EPAP control pressure. The degree of opening of the exhalation valve and the adjustment of the back pressure are preferably matched to one another by means of the monitoring device. In particular, the back pressure is adjusted depending on the degree of opening. The degree of opening can also be adjusted depending on the back pressure. In particular, the matching is designed in such a way that a flushing of the exhaled air from the breathing interface is adjusted. Particularly preferably, the matching results in a preferably complete flushing of the exhaled air. In this case it is possible that the back pressure is also utilized as a flushing pressure in order to flush the exhaled air.

In all embodiments, it is particularly preferred that a regulation of the adjustment of the back pressure and/or a degree of opening of the exhalation valve are/is carried out in real time. In particular, the real-time regulation also includes the detection and/or evaluation of the characteristic variable for the flow within the flow connection. A real-time regulation makes it possible to adjust the back pressure particularly rapidly. As a result, on the one hand, effective protection against contamination can be provided and, on the other hand, a high degree of ventilation quality is achieved by means of the rapid reaction capability of the ventilation system. Particularly preferably, a blower device comprising a highly dynamic blower is provided.

Preferably at least one ventilation parameter is also taken into consideration during the adjustment of the back pressure. Particularly preferably, the demand for respiratory air and/or the respiratory frequency are/is taken into consideration. Other ventilation parameters can also be taken into account, such as, for example, a necessary minimum or maximum ventilation pressure. Particularly preferably, the first ventilation pressure and/or the second ventilation pressure are/is also adjusted or regulated depending on at least one ventilation parameter required for ventilation. In this way, an optimal ventilation quality can be ensured.

In particular, the second ventilation pressure is also adjusted to at least one setpoint pressure required for the exhalation phase. The required setpoint pressure preferably corresponds to a PEEP or a EPAP. Such a setpoint pressure is adjusted, in particular, during valve ventilation.

In this case, the adjustment of the second ventilation pressure to the setpoint pressure takes place, in particular, at a different point in time than the increase to the back pressure. In particular, the increase of the second ventilation pressure to the back pressure takes place before or after the adjustment of the second ventilation pressure to the setpoint pressure. It is also possible that an adjustment of the second ventilation pressure to the setpoint pressure is intermittently interrupted by the adjustment to the back pressure.

It can also be provided that the adjustment of the second ventilation pressure to the setpoint pressure takes place simultaneously with the increase of the second ventilation pressure to the setpoint pressure when the necessary pressure levels are identical or sufficiently similar.

It is possible that the setpoint pressure is adjusted with priority over the back pressure. For example, the back pressure can be adjusted to be lower when the setpoint pressure would otherwise be unfavorably decreased or increased. It can also be provided that the back pressure is temporarily adjusted—in favor of a required setpoint pressure—to a value that permits a backflow of the expiratory flow into the ventilation device. By means of such a prioritization, safe and reliable ventilation can always be ensured. It can also be provided that the back pressure is adjusted with priority over the setpoint pressure.

Preferably, the level and/or the duration and/or the point in time of the back pressure are/is adjusted with consideration for the setpoint pressure for the second ventilation pressure. In this way, the level or the duration of the point in time of the back pressure can be selected in such a way that the necessary setpoint pressure of the second ventilation pressure can be maintained. As a result, the setpoint pressure can be provided without unfavorably influencing the adjustment to the required setpoint pressure.

In all embodiments, it is particularly preferred that the ventilator is operated in an operating mode for valve ventilation without a non-return valve for preventing backflowing exhaled air. As a result, it is possible to switch between valve ventilation and leakage ventilation particularly conveniently and easily, since there is no need to exchange a non-return valve.

Preferably, the flow connection is provided by means of at least one tubing device and by means of at least one device section. The tubing device is designed, in this case, as a tubing device that can be coupled to the ventilation device. The device section is accommodated, in particular, in the ventilation device and is preferably fixedly installed. In particular, the ventilation device includes at least one coupling device for connecting the tubing device. The device section is then located, in particular, between the blower device and the coupling device. The device section can include the coupling device. The exhalation valve, in particular, is disposed on the tubing device.

The characteristic variable for the flow may be detected, in particular, in the device section. For this purpose, the device section can include at least one measuring channel comprising at least one sensor. Preferably, the back pressure is also applied in the device section. In particular, the back pressure may be adjusted in such a way that an entry by the backflowing expiratory flow into the device section is counteracted. A backflowing expiratory flow in the ventilation device is particularly unfavorable, since the ventilation device can generally be cleaned only with a great deal of difficulty. A backflow into the tubing device is relatively unproblematic, however.

The ventilator according to the invention comprises at least one ventilation device. The ventilation device comprises at least one blower device for generating a respiratory gas flow. The ventilation device comprises at least one flow connection, via which the respiratory gas flow can be conveyed by the blower device to a breathing interface. The breathing interface is used, in particular, for coupling the ventilator to a breathing opening of the patient. The ventilation device is suited and designed for adjusting the respiratory gas flow to at least one first ventilation pressure with the aid of the blower device during an inhalation phase of a patient. The ventilation device is suited and designed for adjusting the respiratory gas flow to at least one second ventilation pressure during an exhalation phase. In this case, the ventilation device comprises at least one monitoring device for monitoring backflowing exhaled air. The monitoring device is suited and designed for adjusting at least one characteristic variable for a flow within the flow connection by means of at least one sensor device. The monitoring device is suited and designed for providing, with consideration for the detected variable, at least one back pressure with respect to the backflowing expiratory flow with the aid of a specific increase of the second ventilation pressure by means of the blower device.

The ventilator according to the invention also offers many advantages. It is particularly advantageous that a non-return valve for preventing backflowing exhaled air can be dispensed with. As a result, it is possible to switch between leakage ventilation and valve ventilation without the need to install or remove a non-return valve. The user or caregiver merely needs to connect the appropriate tubing system having the desired exhalation system to the ventilator.

The ventilator comprises, in particular, at least one controllable exhalation valve for discharging exhaled air. In particular, the degree of opening of the exhalation valve is controllable by means of the monitoring device. The monitoring device is suited and designed, in particular, for regulating the degree of opening of the exhalation valve and/or the adjustment of the back pressure in real time. In particular, the ventilator does not comprise a non-return valve for preventing rebreathing into the ventilation device.

BRIEF DESCRIPTION OF THE DRAWINGS

Further advantages and features of the present invention result from the description of the exemplary embodiments which are described in the following with reference to the attached drawings.

In the drawings.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
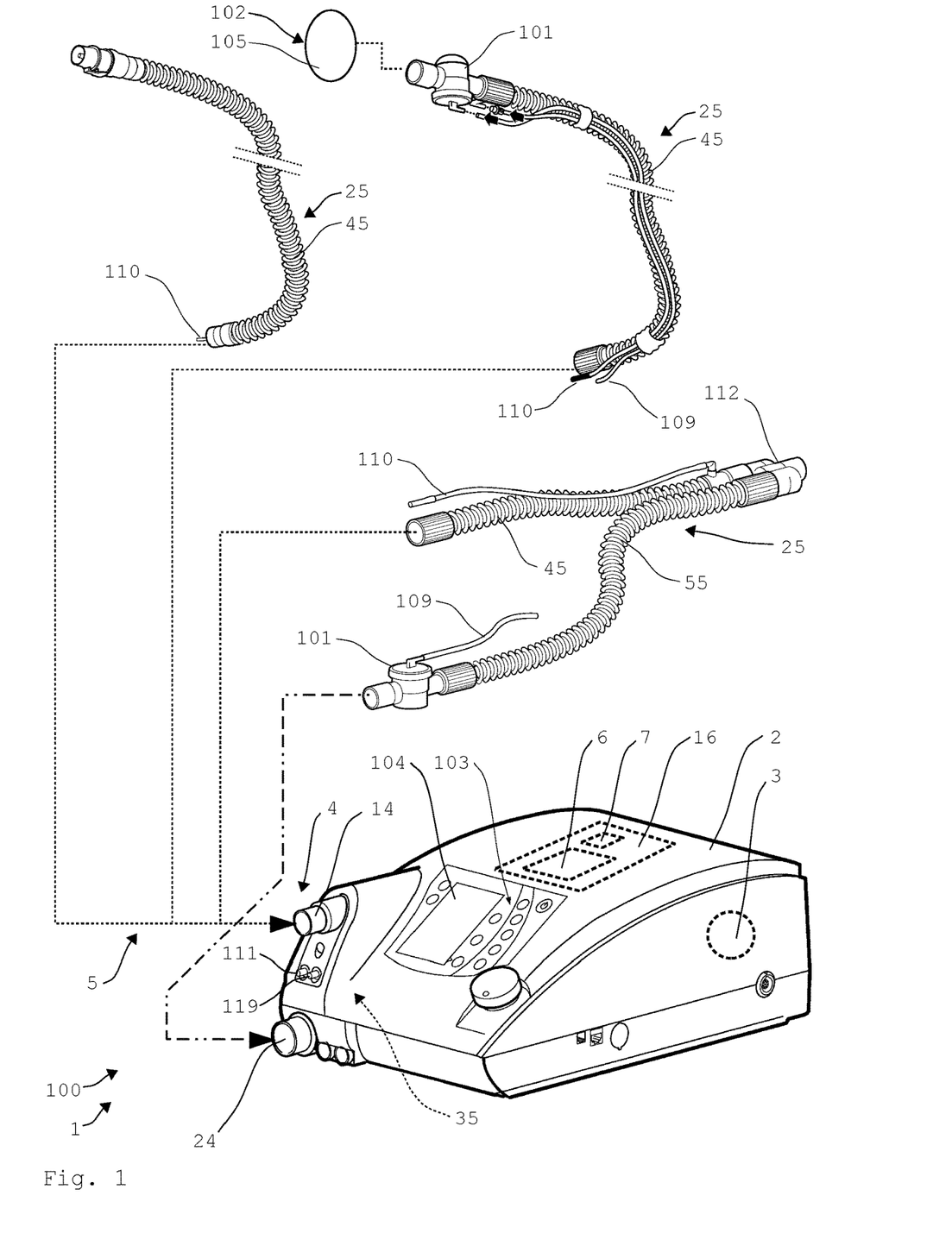
FIG. 1 shows a perspective view of a schematic representation of a ventilator according to the invention comprising various tubing devices.

FIG. 1 shows a ventilator 1 according to the invention, which is designed as a home ventilator 100 or a sleep therapy device. The ventilator 1 can also be utilized, however, as a clinical ventilator 1. The ventilator 1 is operated, in this case, according to the method according to the invention.

The ventilator 1 includes a ventilation device 2 comprising a blower device 3 for generating a respiratory gas flow for ventilation. In addition, by way of example, three different types of tubing devices 25 are shown, which are connectable to the ventilation device 2. The connected tubing device 25, together with a device section 35 (not shown here) in the interior of the ventilation device 2, forms a flow connection 5 between the blower device 3 and a breathing interface 102.

A control device 16 is provided here for controlling or regulating the ventilation device 2 and, in particular, the blower device 3. The operation and adjustment of the ventilator 1 takes place via an operating device 103 comprising a display device 104.

The control device 16 is also operatively connected to a sensor device 7 (not shown here in greater detail). The sensor device 7 comprises one or multiple sensors 17, 27 for detecting ventilation parameters and, preferably, characteristic variables (6') of the respiratory gas flow.

The control device 16 provides, e.g., a necessary minimum pressure and compensates for pressure fluctuations caused by the breathing activity of the user. For example, the control device 16 also detects the present pressure and flow of the ventilation by way of the sensor device 7 and adjusts the power of the blower device 3 accordingly, until a desired ventilation pressure or flow is present.

The ventilation parameters required for adjusting the ventilation device 2 or the blower device 3 as well as the device configuration and/or device software are stored in a memory device of the control device 16.

The ventilator 1 shown here can be designed as a fix-level device or as an automatic-level device. In particular, in this case, the control device 16 regulates to setpoint ventilation parameters which have been individually calculated and established in advance on the basis of the characteristic breathing of a user.

The ventilation device 2 is adapted dynamically and, in particular, depending on the breathing phase of the user in this case. For example, a switch in the breathing phase can be detected with the aid of the control device 16 or sensor device 7, and so a higher or lower pressure can be provided, depending on the breathing phase. In this way, the respiratory gas flow is adjusted to a first ventilation pressure during an inhalation phase of the patient, and is adjusted to a second ventilation pressure during an exhalation phase. In particular, the ventilator 1 reacts to certain breathing events, such as, e.g., snoring, respiratory depression and/or obstructive pressure spikes, with appropriate adjustments of the ventilation parameters.

A breathing interface 102, which is represented highly schematically here, is provided in order to direct the respiratory gas flow to a breathing opening of the user during ventilation. The breathing interface 102 is preferably designed as a patient interface and can be configured, for example, as a full-face mask, as a nasal pillow, as a tube, or as a larynx mask. The breathing interface 102 shown here is a breathing mask 105 designed as a nasal mask. A headgear can be provided for fixing the breathing mask 105 in position.

Different types of tubing devices 25 can be utilized for connecting the breathing interface 102 to the ventilation device 2. The desired tubing device 25 is connected to the ventilation device 2 via a coupling device 4, and so the flow connection 5 is provided between the blower device 3 and the breathing interface 102. The tubing device 25 comprises coupling elements at the particular ends, in order to be connected at the breathing interface 102 and at the coupling device 4.

A tubing device 25 for leakage ventilation is shown with a ventilation tube 45 in the upper left in FIG. 1. For this purpose, a defined opening is provided in the ventilation tube 45 or in the breathing interface 102 and, for example, in the breathing mask 105. The exhaled air and, in particular, the expiratory carbon dioxide are flushed out via this opening. The ventilation tube 45 is fluidically connected to the ventilation device 2 via a first coupling 14 of the coupling device 4.

Shown to the right of and below said ventilation tube are two tubing devices 25 which are used for valve ventilation and comprise an exhalation valve 101. Shown at the bottom is a tubing device 25 comprising a ventilation tube 45 and an exhalation tube 55, a so-called double patient circuit. Such a double patient circuit is utilized, for example, when the expiratory volume must be determined particularly reliably. For this purpose, the exhalation tube 55 is fluidically connected to the ventilation device 2 via a second coupling 24. The two tubes 45, 55 are fluidically connected to the breathing interface 102 via a Y-adapter 112.

The two tubing devices 25 shown at the top are so-called single patient circuits and each comprise a ventilation tube 45, but they do not comprise an exhalation tube 55.

The tubing devices 25 each comprise, in this case, a measuring tube 110 which is fluidically connected to the ventilation device 2 via an inlet port connector 111. In this way, a characteristic variable (6') and, for example, the pressure and/or the flow of the respiratory gas flow can be detected close to the patient. For this purpose, for example, at least one pressure sensor and/or at least one flow sensor, which is fluidically connected to the inlet port connector 111, are/is located in the ventilation device for this purpose. The measuring tube 110 and the inlet port connector 111 can be utilized in this case both for monitoring the ventilation and for monitoring a backflow of the expiratory flow.

The tubing device 25 for valve ventilation comprises a controllable patient valve 101 in this case. The breathing interface 102 and, for example, the breathing mask 105, are connected to the patient valve 101. The patient valve 101 is controlled via a control tube 109 which is fluidically connected to the patient valve 101 and to a control connector 119 of the ventilation device 2. Inhalation and exhalation are controlled by means of the exhalation valve 101. When a tubing device 25 is utilized for valve ventilation, no patient/ventilator interfaces having leakage openings may be used, in general.

A specific control pressure and, for example, an EPAP or PEEP control pressure, is applied to the control tube 109 by means of the ventilation device 2. As a result, the patient valve 101 can be opened or closed at the desired time.

The tubing devices 25 shown here can be interchanged depending on the patient or depending on the ventilation need. If a tubing device 25 is utilized for valve ventilation, and if no further measures are taken, an undesirable rebreathing into the ventilation device 2 can occur. A monitoring device 6 is provided here in order to protect the ventilation device 2 against the backflowing exhaled air. The monitoring device 6 is part of the control device 16 or is integrated into the control device in this case.

The monitoring device 6 monitors the respiratory flow of the patient flowing back into the flow connection 5. If a corresponding backflow is detected, which would result in exhaled air entering the ventilation device 2, a back pressure is generated. An entry by the exhaled air into the ventilation device 2 is counteracted by means of the back pressure. The prevention of the backflow by means of the back pressure is described in greater detail with reference to the following figures.

It is therefore possible to switch between leakage ventilation and valve ventilation by easily and conveniently replacing the tubing devices 25, without the need for conversions in order to prevent the backflow. It is particularly advantageous that the ventilator 1 does not comprise a non-return valve in this case, which would have to be installed or removed when switching the exhalation system. Such a non-return valve must not be utilized, in general, with leakage ventilation, so that backflow is possible during exhalation.

Figure 2:
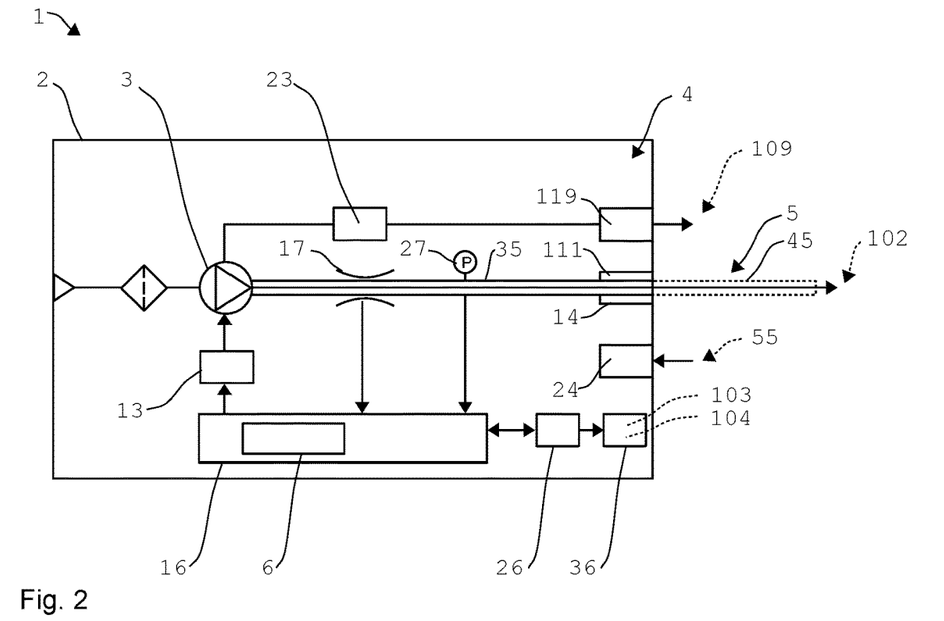
FIG. 2 shows a highly schematic representation of a ventilator according to the invention.

FIG. 2 shows a highly schematic representation of the ventilator 1. The operative connections between the individual components are represented here in a highly schematic and simplified manner as arrows.

The ventilation device 2 comprises a blower device 3 for generating the respiratory gas flow. The respiratory gas flow is guided to the first coupling 14 via a device section 35 located in the ventilation device 2. From there, the respiratory gas flow is guided further to the breathing interface 102 via a ventilation tube 45. The device section 35 and the ventilation tube 45 provide the flow connection 5 in this case.

A flow sensor 17 and a pressure sensor 27 are provided here in order to detect a characteristic variable (6') for a flow within the flow connection 5. The characteristic variable (6') for the flow is the volumetric flow rate and/or the pressure in this case. The flow sensor 17 and the pressure sensor 27 are fluidically connected to the flow connection 5 in this case, and so the pressure or volumetric flow rate present there can be detected. The detected values for the pressure and the volumetric flow rate are provided to the control device 16 or the monitoring device 6, and so these can appropriately control or regulate the blower device 3.

The flow sensor 17 and the pressure sensor 27 can also be fluidically connected to the inlet port connector 111, and so the pressure or the flow can also be detected via a connected measuring tube 110.

A driver device 13 is provided here in order to control the blower device 3 by means of the control device 16 or the monitoring device 6. In this case, the control device 16 takes into account at least one device configuration as well as requirements for adjusting certain ventilation parameters.

A user interface 36 comprising an operating device 103 and a display device 104 is provided here for the purpose of implementing adjustments for the device configuration and/or for adjusting ventilation parameters. The entries that are carried out are provided to the control device 16 via a user interface controller 26.

In addition, the respiratory gas flow generated by the blower device 3 can also be utilized as control pressure for an exhalation valve 101. For this purpose, the respiratory gas flow is guided to the patient valve via the control connector 119 and a control tube 109 connected thereto. An actuator 23 is provided here in order to enable the control pressure to be specifically adjusted. This actuator adjusts the desired EPAP or PEEP control pressure, for example. The actuator 23 is operatively connected, in particular, to the control device 16.

The ventilation device 2 also comprises, in this case, a second coupling 24 for an exhalation tube 55. The exhaled air flowing in there is released into the surroundings by means of the ventilation device 2.

The monitoring device 6 monitors the flow within the flow connection 5 in order to protect the ventilation device 2 against backflowing exhaled air. For this purpose, the volumetric flow rate is detected by means of the flow sensor 17. If the volumetric flow rate has a value below a threshold value or if a negative volumetric flow rate is detected, the monitoring device 6 regulates the blower device 3 to an appropriate back pressure.

In this case, it can be provided that the back pressure is built up only after a latency which is dynamically established. The latency describes the time, in this case, that the backflowing expiratory flow requires in order to flow through the ventilation tube 45. In this case, the monitoring device accounts for, for example, a stored dead space volume of the ventilation tube 45 in order to establish the latency. In addition, the monitoring device 6 also accounts for the pressure and/or the volumetric flow rate and/or a flow velocity in order to establish the latency.

In this way, the back pressure can be specifically built up when the expiratory flow has flowed through the ventilation tube 45 but has not yet entered the ventilator 2 or the device section 35. The latency can also be selected in such a way that the backflowing expiratory flow flows through the ventilation tube 45 only partially or not at all.

The level of the back pressure is adjusted, in this case, by means of the monitoring device in such a way that the back pressure is sufficiently high to hold back the expiratory flow but does not disadvantageously influence the required ventilation. In this case, the monitoring device 6 accounts for at least one ventilation parameter and, for example, a PEEP and/or an EPAP. The value detected by means of the pressure sensor 27 can be utilized for monitoring or regulating the back pressure.

The monitoring device 6 can also evaluate the ascertained values for the volumetric flow rate in order to evaluate a course of inhalation and exhalation phases over time. In this way, statements can also be made regarding the patient's respiratory frequency and/or demand for respiratory air on the basis of the detected variable (6').

During exhalation, the respiratory air exhaled by the patient under a corresponding pressure against the respiratory gas flow supplied by the ventilation device 2 results in contra-directional gas flows in the flow connection 5. The inflow of fresh respiratory gas from the ventilation device 2 or the ventilation tube 45 decelerates during exhalation. This deceleration is determined by sensors, in particular by means of the flow sensor 17, in the form of a correspondingly reduced volumetric flow rate. The monitoring device 6 therefore detects the rebreathing in this case on the basis of a reduced volumetric flow rate.

The monitoring device 6 then determines the necessary adjustments of the blower device 3 and, for example, the necessary adjustment of the blower speed. In order to regulate the back pressure, the monitoring device 6 can not only account for the detected volumetric flow rate, but also the pressure detected by the pressure sensor 27. It is also possible that the monitoring device 6 accounts for the patient's respiratory frequency and/or demand for respiratory air in the regulation of the blower device 3 during the adjustment of the back pressure. In this way, a back pressure can be generated at the outlet of the device section 35, which effectively prevents rebreathing and simultaneously provides for an optimal respiratory quality.

In order to be able to ensure an optimal flushing flow, by means of which the exhaled air can be preferably completely flushed out during the exhalation phase, the exhalation valve 101 can also be controlled by means of the monitoring device 6 in this case. In this case, a degree of opening of the exhalation valve 101, in particular, is adjusted. In this way, a particularly large amount of the $CO_2$-rich exhaled air can be flushed out. For this purpose, the PEEP control pressure is regulated to the required degree of opening by means of the actuator 23.

The blower device 3 is preferably adjusted during the exhalation phase in such a way that a desired flushing is achieved. In this case, in particular, the flushing pressure and the degree of opening of the exhalation valve 101 are matched to each other. While the volume is monitored, the degree of opening of the exhalation valve 101 and, intermittently, the second ventilation pressure are controlled by means of the blower device 3 in such a way that the CO2-enriched exhaled air is preferably completely flushed out by the time the subsequent inhalation phase begins.

Figure 3:
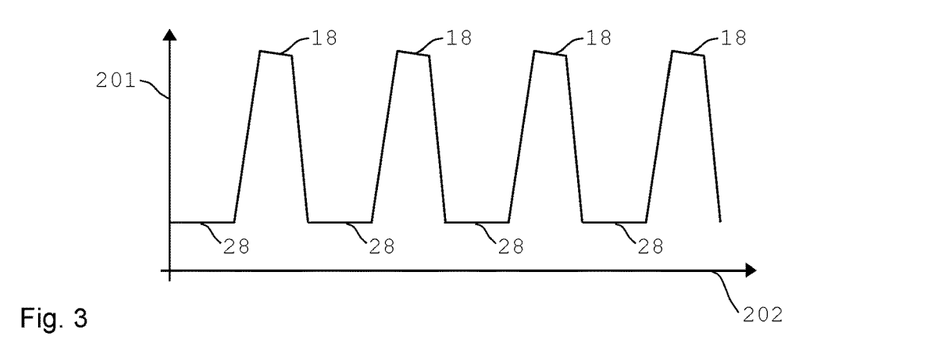
FIG. 3 shows a highly schematic representation of a pressure curve without back pressure.

FIG. 3 shows a highly schematically represented pressure curve during an exemplary ventilation. For this purpose, the pressure 201 is plotted against the time 202. In this case, a first ventilation pressure 18 is built up during a patient's inhalation phase, in order to supply the patient with a required volume of fresh respiratory gas under a required pressure. During the exhalation phase, the respiratory gas flow is then adjusted to a second ventilation pressure which supports the patient's exhalation process. The ventilation shown here therefore includes a cyclic change of the ventilation pressure during the inhalation phase and the exhalation phase.

The second ventilation pressure is adjusted by means of the monitoring device 6 to a setpoint pressure required for the ventilation. The setpoint pressure is adjusted to a desired PEEP or an EPAP, for example.

Figure 4:
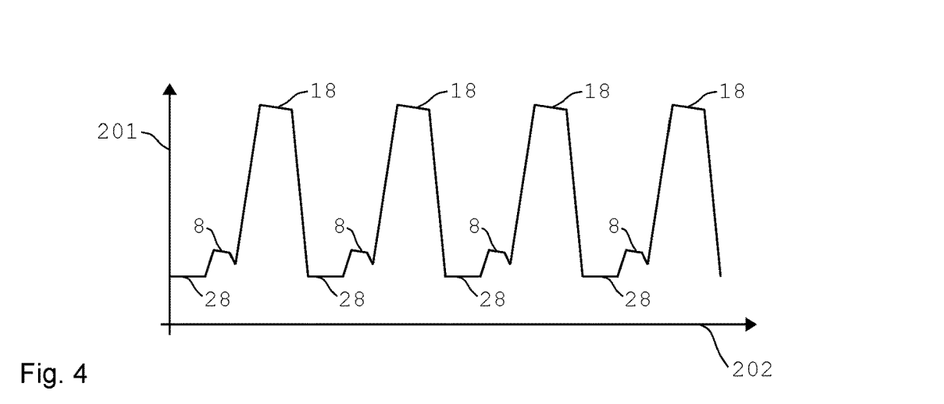
FIG. 4 shows a highly schematic representation of a pressure curve with back pressure.

FIG. 4 shows a highly schematic pressure curve of another ventilation. In this case, a back pressure 8 was intermittently applied according to the method presented here for protecting the ventilation device against backflowing exhaled air. The back pressure 8 in this case is a specific increase of the second ventilation pressure 28. The level of the pressure or the duration and the point in time of the back pressure 8 are established by the monitoring device 6 in this case. In this case, the monitoring device 6 accounts for the detected volumetric flow rate and the required ventilation parameters, in particular.

In the example shown here, the second ventilation pressure 28 is raised toward the end of the exhalation phase to a higher pressure level in order to provide the back pressure 8. As a result, the back pressure 8 can be specifically built up when the backflowing expiratory flow reaches an extent that could result in an undesirable inflow into the ventilation device 2. Alternatively, the back pressure can be adjusted as needed and independently of the first or the second ventilation pressure. The back pressure 8 can be regulated upward, independently of the respiratory phases, when the monitoring device 6 ascertains a commencing or impending rebreathing into the device.

The back pressure 8 is supplanted by the first ventilation pressure in this case, which is applied in the next inhalation phase. The back pressure 8 can also be reduced back down to the pressure level of the second ventilation pressure, or lower. The second ventilation pressure 28 is then supplanted by the first ventilation pressure after the end of the exhalation phase.

The back pressure can also be higher, for example, than the first and the second pressures. The first and the second pressures can be at least intermittently identical.

The invention presented here has the advantage that rebreathing during valve ventilation is not prevented by means of a non-return valve, but rather by means of the suitable regulation of the blower device 3 or by the actuator 23 for the PEEP control pressure. As a result, a switch between leakage ventilation and valve ventilation is possible in a particularly user-friendly manner and without conversions.

LIST OF REFERENCE NUMBERS

1 ventilator
2 ventilation device
3 blower device
4 coupling device
5 flow connection
6 monitoring device
7 sensor device
8 back pressure
13 driver device
14 coupling
16 control device
17 flow sensor
18 first ventilation pressure
23 actuator
24 coupling 25 tubing device
26 user interface controller
27 pressure sensor
28 second ventilation pressure
35 device section
36 user interface
45 ventilation tube
55 exhalation tube
100 home ventilator
101 exhalation valve
102 breathing interface
103 operating device
104 display device
105 breathing mask
109 control tube
110 measuring tube
111 inlet port connector
112 Y-adapter
119 control connector
202 time
201 pressure

What is claimed is:

1. A method for protecting a ventilation device of a ventilator against backflowing exhaled air, wherein the method comprises generating a respiratory gas flow by at least one blower device and guiding the flow via at least one flow connection to a breathing interface, the respiratory gas flow being adjusted with the aid of a control device to at least one first ventilation pressure during an inhalation phase of a patient and to at least one second ventilation pressure during an exhalation phase, and wherein at least one characteristic variable for a flow within the at least one flow connection is detected by at least one monitoring device for monitoring backflowing exhaled air, and at least one back pressure with respect to the backflowing expiratory flow is adjusted by a specific increase of the ventilation pressure with consideration for the at least one characteristic variable, whereby undesirable rebreathing into the ventilation device is counteracted by the back pressure.

2. The method of claim 1, wherein a volumetric flow rate is detected at the at least one characteristic variable for a flow.

3. The method of claim 1, wherein an adjustment of a level and/or a duration of the back pressure and/or a point in time of generation of the back pressure is carried out with consideration for the at least one characteristic variable.

4. The method of claim 1, wherein the back pressure is applied when the at least one characteristic variable indicates that there is a flow within the at least one flow connection that is below a threshold value and/or indicates that there is a negative flow.

5. The method of claim 1, wherein the back pressure is applied after a latency, and wherein the latency accounts for a flow duration of the backflowing expiratory flow through a tubing device which is coupled to the ventilation device.

6. The method of claim 5, wherein the latency is dynamically calculated and a dead space volume of a coupled tubing device stored in the monitoring device and/or at least one value of a negative flow are taken into account.

7. The method of claim 1, wherein the ventilator is operated in an operating mode for valve ventilation, and wherein, for this purpose, at least one exhalation valve is opened during the exhalation phase of the patient to discharge exhaled air.

8. The method of claim 7, wherein a degree of opening of the exhalation valve is controllable, and wherein the degree of opening of the exhalation valve and an adjustment of the back pressure are matched to each other by the monitoring device, whereby flushing of the exhaled air is adapted.

9. The method of claim 7, wherein a regulation of an adjustment of the back pressure and/or a degree of opening of an exhalation valve are/is carried out in real time.

10. The method of claim 9, wherein at least one ventilation parameter is further taken into account during the adjustment of the back pressure.

11. The method of claim 10, wherein the at least one ventilation parameter comprises at least one of a demand for respiratory air and respiratory frequency.

12. The method of claim 1, wherein the second ventilation pressure is adjusted to at least one setpoint pressure for a PEEP or an EPAP required for the exhalation phase.

13. The method of claim 12, wherein the adjustment of the second ventilation pressure to the setpoint pressure takes place at a different point in time than an increase of the ventilation pressure to the back pressure.

14. The method of claim 12, wherein the setpoint pressure is adjusted with priority over the back pressure.

15. The method of claim 12, wherein a level and/or a duration and/or a point in time of the back pressure is adjusted with consideration for the setpoint pressure.

16. The method of claim 1, wherein the ventilator is operated in an operating mode for valve ventilation without a non-return valve for hindering backflowing exhaled air.

17. The method of claim 1, wherein the at least one flow connection is provided by at least one tubing device which can be coupled to the ventilation device and by at least one device section accommodated in the ventilation device, and wherein the at least one characteristic variable is detected in the at least one device section and/or wherein the back pressure is applied in the at least one device section.

18. A ventilator, wherein the ventilator comprises at least one ventilation device including at least one blower device for generating a respiratory gas flow, and at least one flow connection via which the respiratory gas flow can be guided by the blower device to a breathing interface, the ventilation device being suited and designed for adjusting the respiratory gas flow with the aid of the blower device to at least one first ventilation pressure during an inhalation phase and to at least one second ventilation pressure during an exhalation phase, and wherein the ventilation device further comprises at least one monitoring device for monitoring backflowing exhaled air, which monitoring device is suited and designed for detecting at least one characteristic variable for a flow within the at least one flow connection by at least one sensor device and for providing, with consideration for the at least one characteristic variable, at least one back pressure with respect to the backflowing expiratory gas flow with the aid of a specific increase of the ventilation pressure by the blower device, whereby undesirable rebreathing into the ventilation device is counteracted by the back pressure.

19. A ventilator, wherein the ventilator comprises at least one ventilation device including at least one blower device for generating a respiratory gas flow, and at least one flow connection via which the respiratory gas flow can be guided by the blower device to a breathing interface, and wherein a device outlet port in an area of a coupling is designed for optional utilization of a tubing system having a leakage opening and a tubing system comprising a patient valve without carrying out a conversion of a device outlet port in the area of the coupling, wherein there is no non-return valve in the area of the device outlet port, whereby rebreathing in the area of the at least one flow connection is avoided, wherein the ventilator comprises at least one ventilation device which includes at least one blower device for generating a respiratory gas flow, and at least one flow connection via which the respiratory gas flow can be guided by the blower device to a breathing interface, and wherein the at least one ventilation device is suited and designed for adjusting the respiratory gas flow with the aid of the blower device to at least one first ventilation pressure during an inhalation phase and to at least one second ventilation pressure during an exhalation phase, the at least one ventilation device comprising at least one monitoring device for monitoring backflowing exhaled air, which monitoring device is suited and designed for detecting at least one characteristic variable for a flow within the at least one flow connection by at least one sensor device and for at least intermittently providing, with consideration for the at least one characteristic variable, a back pressure with respect to a backflowing expiratory flow with the aid of a specific increase of the at least one second ventilation pressure by the blower device.

\* \* \* \* \*